US012310929B2

(12) United States Patent
Blaugrund et al.

(10) Patent No.: US 12,310,929 B2
(45) Date of Patent: May 27, 2025

(54) USE OF RASAGILINE FOR THE TREATMENT OF RESTLESS LEGS SYNDROME

(71) Applicants: Eran Blaugrund, Rehovot (IL); Ruth Levy, Tel Aviv (IL)

(72) Inventors: Eran Blaugrund, Rehovot (IL); Ruth Levy, Tel Aviv (IL)

(73) Assignee: TEVA PHARMACEUTICAL INDUSTRIES, LTD., Petah Tikva (IL)

( * ) Notice: Subject to any disclaimer, the term of this patent is extended or adjusted under 35 U.S.C. 154(b) by 885 days.

(21) Appl. No.: 17/399,753

(22) Filed: Aug. 11, 2021

(65) Prior Publication Data

US 2021/0386690 A1    Dec. 16, 2021

Related U.S. Application Data

(63) Continuation of application No. 17/306,106, filed on May 3, 2021, now abandoned, which is a continuation of application No. 17/152,514, filed on Jan. 19, 2021, now abandoned, which is a continuation of application No. 17/065,811, filed on Oct. 8, 2020, now abandoned, which is a continuation of application No. 16/913,633, filed on Jun. 26, 2020, now abandoned, which is a continuation of application No. 16/815,979, filed on Mar. 11, 2020, now abandoned, which is a continuation of application No. 16/696,568, filed on Nov. 26, 2019, now abandoned, which is a continuation of application No. 16/543,164, filed on Aug. 16, 2019, now abandoned, which is a continuation of application No. 16/405,468, filed on May 7, 2019, now abandoned, which is a continuation of application No. 16/233,046, filed on Dec. 26, 2018, now abandoned, which is a continuation of application No. 16/102,148, filed on Aug. 13, 2018, now abandoned, which is a continuation of application No. 15/895,962, filed on Feb. 13, 2018, now abandoned, which is a continuation of application No. 15/697,935, filed on Sep. 7, 2017, now abandoned, which is a continuation of application No. 15/096,038, filed on Apr. 11, 2016, now abandoned, which is a continuation of application No. 14/524,993, filed on Oct. 27, 2014, now abandoned, which is a continuation of application No. 11/731,493, filed on Mar. 30, 2007, now Pat. No. 8,946,300.

(60) Provisional application No. 60/788,617, filed on Apr. 3, 2006.

(51) Int. Cl.
| | | |
|---|---|---|
| A61K 31/135 | (2006.01) | |
| A61K 31/16 | (2006.01) | |
| A61K 31/428 | (2006.01) | |
| A61P 21/00 | (2006.01) | |
| A61P 25/00 | (2006.01) | |
| A61P 25/08 | (2006.01) | |
| A61P 25/14 | (2006.01) | |
| A61P 43/00 | (2006.01) | |

(52) U.S. Cl.
CPC ............ *A61K 31/135* (2013.01); *A61K 31/16* (2013.01); *A61K 31/428* (2013.01); *A61K 2300/00* (2013.01)

(58) Field of Classification Search
CPC .... A61K 31/135; A61K 31/16; A61K 31/428; A61K 2300/00; A61P 25/00; A61P 25/14; A61P 25/08; A61P 21/00; A61P 43/00
See application file for complete search history.

(56) References Cited

U.S. PATENT DOCUMENTS

| | | |
|---|---|---|
| 4,843,086 A | 6/1989 | Griss et al. |
| 5,387,612 A | 2/1995 | Youdim et al. |
| 5,444,095 A | 8/1995 | Tatton et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,622,720 A | 4/1997 | Collin |
| 5,668,181 A | 9/1997 | Youdim et al. |
| 5,744,500 A | 4/1998 | Youdim et al. |
| 5,767,164 A | 6/1998 | Tatton et al. |
| 5,786,390 A | 7/1998 | Youdim et al. |
| 5,844,003 A | 12/1998 | Tatton et al. |
| 5,891,923 A | 4/1999 | Youdim et al. |
| 6,126,968 A | 10/2000 | Peskin et al. |
| 6,277,886 B1 | 8/2001 | Levy et al. |

(Continued)

FOREIGN PATENT DOCUMENTS

| | | |
|---|---|---|
| CA | 2644750 | 11/2011 |
| EP | 0 538 134 | 4/1993 |

(Continued)

OTHER PUBLICATIONS

Aug. 1, 2014 Response to Office Action issued in the U.S. Appl. No. 11/731,493.
Apr. 1, 2014 Office Action issued in the U.S. Appl. No. 11/731,493.
Jul. 25, 2012 Response to Jul. 6, 2012 Advisory Action issued in U.S. Appl. No. 11/731,493.
Jul. 6, 2012 Advisory Action issued Nov. 23, 2010 in the U.S. Appl. No. 11/731,493.

(Continued)

*Primary Examiner* — Sun Jae Yoo

(74) *Attorney, Agent, or Firm* — Gary J. Gershik

(57) ABSTRACT

Disclosed are methods for the treatment of Restless Legs Syndrome comprising administering an amount of R(+)-N-propargyl-1-aminoindan or a pharmaceutically acceptable salt thereof.

18 Claims, No Drawings

(56) References Cited

U.S. PATENT DOCUMENTS

| | | |
|---|---|---|
| 6,316,504 B1 | 11/2001 | Youdim et al. |
| 6,462,222 B1 | 10/2002 | Chorev et al. |
| 6,630,514 B2 | 10/2003 | Youdim et al. |
| 6,635,667 B2 | 10/2003 | Thomas |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Sterling et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 7,968,749 B2 | 6/2011 | Frenkel et al. |
| 8,080,584 B2 | 12/2011 | Safadi et al. |
| 8,143,315 B2 | 3/2012 | Stahl et al. |
| 8,188,149 B2 | 5/2012 | Lendavi et al. |
| 8,334,409 B2 | 12/2012 | Frenkel |
| 8,569,379 B2 | 10/2013 | Petit et al. |
| 8,614,252 B2 | 12/2013 | Frenkel et al. |
| 8,691,872 B2 | 4/2014 | Linengreen et al. |
| 8,759,382 B2 | 6/2014 | Falb et al. |
| 8,809,310 B2 | 8/2014 | Poewe |
| 8,946,300 B2 * | 2/2015 | Blaugrund ............... A61P 21/00 514/649 |
| 9,308,182 B2 | 4/2016 | Fitzer-Attas et al. |
| 2001/0053777 A1 | 12/2001 | Brecht |
| 2004/0010038 A1 | 1/2004 | Blaugrund et al. |
| 2004/0052843 A1 | 3/2004 | Lerner et al. |
| 2004/0127577 A1 | 7/2004 | Blaugrund et al. |
| 2006/0018957 A1 | 1/2006 | Lerner et al. |
| 2006/0094783 A1 | 5/2006 | Youdim |
| 2006/0188581 A1 | 8/2006 | Peskin |
| 2007/0100001 A1 | 5/2007 | Youdim |
| 2007/0112217 A1 | 5/2007 | Frenkel |
| 2007/0232700 A1 | 10/2007 | Blaugrund et al. |
| 2008/0146676 A1 | 6/2008 | Frenkel et al. |
| 2008/0161408 A1 | 7/2008 | Frenkel et al. |
| 2009/0062400 A1 | 3/2009 | Oron et al. |
| 2009/0111892 A1 | 4/2009 | Patashnik et al. |
| 2009/0181086 A1 | 7/2009 | Safadi et al. |
| 2009/0312436 A1 | 12/2009 | Levy et al. |
| 2009/0318564 A1 | 12/2009 | Frenkel et al. |
| 2010/0008983 A1 | 1/2010 | Safadi et al. |
| 2010/0010095 A1 | 1/2010 | Frenkel |
| 2010/0010098 A1 | 1/2010 | Elffrink |
| 2010/0029987 A1 | 2/2010 | Allegrini et al. |
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189787 A1 | 7/2010 | Safadi et al. |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |
| 2013/0089610 A1 | 4/2013 | Safadi et al. |
| 2013/0089611 A1 | 4/2013 | Ulanenko et al. |
| 2013/0089612 A1 | 4/2013 | Safadi et al. |
| 2013/0345310 A1 | 12/2013 | Rimkus et al. |
| 2014/0051767 A1 | 2/2014 | Fitzer-Attas et al. |
| 2014/0186514 A1 | 7/2014 | Safadi et al. |
| 2014/0243418 A1 | 8/2014 | Levy et al. |
| 2014/0364506 A1 | 12/2014 | Bahar et al. |
| 2015/0031774 A1 | 1/2015 | Patashnik et al. |
| 2015/0038744 A1 | 2/2015 | Frenkel et al. |
| 2015/0045445 A1 | 2/2015 | Frenkel et al. |
| 2015/0080441 A1 | 3/2015 | Blaugrund et al. |
| 2016/0317471 A1 | 11/2016 | Blaugrund et al. |
| 2021/0251921 A1 | 8/2021 | Blaugrund et al. |

FOREIGN PATENT DOCUMENTS

| | | |
|---|---|---|
| EP | 0 436 492 A2 | 6/1994 |
| EP | 2 011 488 | 1/2009 |
| JP | 2005 060370 A | 3/2005 |
| WO | WO 95/11016 | 4/1995 |
| WO | WO 95/18617 | 7/1995 |
| WO | WO 96/37199 | 11/1996 |
| WO | WO 97/12583 | 4/1997 |
| WO | WO 98/02152 | 1/1998 |
| WO | WO 2003/072055 | 9/2003 |
| WO | WO 2004/045515 | 6/2004 |
| WO | WO 2005/102300 | 11/2005 |
| WO | WO 2006/057912 | 6/2006 |
| WO | WO 2007/073325 | 6/2007 |
| WO | WO 2007/101400 | 9/2007 |
| WO | WO 2007/117431 | 10/2007 |
| WO | WO 2009/081148 | 7/2009 |
| WO | WO 2009/122301 | 10/2009 |
| WO | WO 2009/152777 | 12/2009 |
| WO | WO 2010/007181 | 1/2010 |
| WO | WO 2010/013048 | 2/2010 |
| WO | WO 2010/049379 | 5/2010 |
| WO | WO 2010/070090 | 6/2010 |
| WO | WO 2011/003938 | 1/2011 |
| WO | WO 2011/009873 | 1/2011 |
| WO | WO 2011/010324 | 1/2011 |
| WO | WO 2013/105092 | 7/2013 |

OTHER PUBLICATIONS

Jun. 25, 2012 Response to Office Action issued Apr. 25, 2012 in the U.S. Appl. No. 11/731,493.

Office Action issued Apr. 25, 2012 in the U.S. Appl. No. 11/731,493.

Feb. 9, 2012 Response to Office Action issued Nov. 9, 2011 in the U.S. Appl. No. 11/731,493.

Office Action issued Nov. 9, 2011 in the U.S. Appl. No. 11/731,493.

Dec. 23, 2010 Response to Advisory Action issued Nov. 23, 2010 in the U.S. Appl. No. 11/731,493.

Advisory Action issued Nov. 23, 2010 in the U.S. Appl. No. 11/731,493.

Sep. 2, 2010 Response to Office Action issued Mar. 29, 2010 in the U.S. Appl. No. 11/731,493.

Office Action issued Mar. 29, 2010 in the U.S. Appl. No. 11/731,493.

Dec. 18, 2009 Response to Office Action issued Sep. 17, 2009 in the U.S. Appl. No. 11/731,493.

Office Action issued Sep. 17, 2009 in the U.S. Appl. No. 11/731,493.

Office Action issued May 1, 2009 in the U.S. Appl. No. 11/731,493.

Extended European Search Report of European Application No. EP 07754738, issued Jun. 3, 2009.

Aug. 28, 2008 International Search Report for PCT International Application No. PCT/US07/08261.

International Preliminary Report on Patentability and the WrittenOpinion of the International Searching Authority for International Application No. PCT/US07/08261, issued Oct. 28, 2008.

Sep. 17, 2009 Official Action issued in European Application No. EP 07754738.8.

Jan. 18, 2010 Amendment filed in response to the Sep. 17, 2009 Official Action issued in European Application No. EP 07754738.8.

Oct. 25, 2010 Response to Apr. 13, 2010 Official Action issued In connection with Chinese Application No. 200780011792. 0 (with English Translation of claims send to associates for filing).

Aug. 17, 2011 Official Action issued in connection with Chinese Application No. 200780011792.0.

Oct. 26, 2011 Response to Aug. 17, 2011 Official Action issued In connection with Chinese ApplicationNo. 200780011792.0.

May 5, 2011 Official Action issued in European Application No. EP 07754738.8.

Aug. 15, 2011 Amendment filed in response to the May 5, 2011 Official Action issued in European Application No. EP 07754738.8.

(56) References Cited

OTHER PUBLICATIONS

Feb. 24, 2012 Official Action issued in European Application No. EP 07754738.8.
Jun. 29, 2012 Response to Feb. 24, 2012 Official Action issued in European Application No. EP 07754738.8.
Oct. 11, 2013 Official Action issued in European Application No. EP 07754738.8.
Apr. 10, 2014 Written Decision issued in European Application No. EP 07754738.8.
Mar. 31, 2014 Minutes of Oral Proceedings issued in European Application No. EP 07754738.8.
May 6, 2010 Official Action issued in New Zealand Application No. 571591.
Apr. 13, 2010 Official Action issued in connection with Chinese Application No. 200780011792.0.
Aug. 9, 2011 Office Action issued by the New Zealand Patent Office connection with New Zealand Patent Application No. 571591.
Response to Aug. 9, 2011 Office Action issued by the New Zealand Patent Office in connection with New Zealand Patent Application No. 571591.
Dec. 21, 2011 Office Action issued by the Australian Patent Office in connection with Australian Patent Application No. 2007235517.
Dec. 20, 2012 Response to Dec. 21, 2011 Office Action issued by the Australian Patent Office in connection with Australian Patent Application No. 2007235517.
Feb. 29, 2012 Third Office Action was issued by the Chinese Patent Office in connection with Chinese Application No. 200780011792.0.
May 15, 2012 Response to Feb. 29, 2012 Third Office Action was Issued by the Chinese Patent Office in connection with Chinese Application No. 200780011792.0.
Aug. 12, 2012 Office Action issued by the Japanese Patent Office in connection with Japanese Patent Application No. 2009-504260.
Response to Aug. 21, 2012 Office Action issued by the Japanese Patent Office in connection with Japanese Patent Application No. 2009-504260.
Dec. 18, 2012 Decision of Rejection issued by the Japanese Patent Office in connection with Japanese Patent Application No. 2009-504260.
Apr. 18, 2013 Request for Appeal filed in Response to Dec. 18, 2012 Decision of Rejection issued by the Japanese Patent Office in connection with Japanese Patent Application No. 2009-504260.
Jun. 3, 2014 Office Action issued by the Japanese Patent Office in connection with Japanese Patent Application No. 2013-087636.
Mar. 20, 2013 Official Action issued by the Canadian Patent Office in connection with Canadian Patent Application No. 2,646,250.
Sep. 20, 2013 Response to Mar. 20, 2013 Official Action issued by the Canadian Patent Office in connection with Canadian Patent Application No. 2,646,250.
Dec. 16, 2013 Official Action issued by the Canadian Patent Office in connection with Canadian Patent Application No. 2,646,250.
Jun. 16, 2014 Response to Dec. 16, 2013 Official Action issued the Canadian Patent Office in connection with Canadian Patent Application No. 2,646,250.
Mar. 6, 2013 Office Action issued by the Mexican Patent Office in connection with Mexican Patent Application No. MX/a/2008/012781.
Apr. 26, 2013 Response to Mar. 6, 2013 Office Action issued by The Mexican Patent Office in connection with Mexican Patent Application No. MX/a/2008/012781.
Jan. 15, 2015 Office Action issued by the Japanese Patent Office in connection with Japanese Patent Application No. 2009-504260.
Sep. 25, 2014 Official Action issued by the Canadian Patent Office in connection with Canadian Patent Application No. 2,656,250.
Mar. 25, 2015 Response to Sep. 25, 2014 Official Action issued by the Canadian Patent Office in connection with Canadian Patent Application No. 2,646,250.
Apr. 13, 2015 Response to Jan. 13, 2015 Office Action filed with Japanese Patent Office in connection with Japanese Patent Application No. 2009-504260.
May 21, 2015 Office Action issued by the Canadian Patent Office in connection with Canadian Patent Application No. 2,646,250.
Allen R.P., "Augmentation of the Restless Legs Syndrome with Carbidopal/Levodopa," Sleep, 1996, 19 (3) :205-213.
Ancoli-Israel et al., "Periodic Limb Movements in Sleep in Community-Dwelling Elderly," Sleep, 14(6) :496-500.
Azilect®, Physician's Desk Reference (2006), 60th Edition, Thomson Healthcare.
Braasch, et al., "Novel antisense and peptide nucleic acid strategies for controlling gene expression," Biochemistry (2002) 41 (14) :4503-4510.
Desautels et al. "Evidence for a genetic association between monoamine oxidase A and restless legs syndrome", Neurology, 2002, vol. 59, Issue 2, pp. 215-219.
Dinesin H. et al., Weight Gain During Treatment With Valproate, Acta. Neurol. Scan., 1984, 70 (2) :65-69.
Dooley M. et al., Pramipexole: A Review of Its Use in the Management of Early and Advanced Parkinson's Disease, Drugs Aging, Jun. 1998, 12 (6) :495-514.
Finberg et al., "Selective Irreversible Propargyl Derivative Inhibitors of Monoamine Oxidase (MAO) without the Cheese Effect", Chem. Abstracts, 1981, 94:2024.
Finberg et al., "Modification of Blood Pressure and Nictitating Membrane Response to Sympathetic Amides by Selective Monoamide Oxidase Inhibitors, Types A and B, in the Cat" Chem. Abstracts, 1985, 103: 81618.
Finberg and Youdim, "Modification of Blood Pressure and Nictitating Membrane Response to Sympathetic Amines by Selective Monoamine Oxidase Inhibitors," Brit. J. Pharmac., 1985, 85 (2) : 541-546.
Fox, G.N., Restless Legs Syndrome, American Family Physician, Jan. 1986, 33 (1) :147-52.
Fulda et al. "Emerging Drugs for Restless Legs Syndrome" Expert Opinion on Emerging Drugs, Ashley Publications, GB, vol. 10, No. 3, Jan. 1, 2005, pp. 537-552.
Guilleminault C. et al., Dopaminergic Treatment of Restless Legs and Rebound Phenomenon, Neurology, 1993, 43 (2) :445.
Grewel et al. (2002) "Treatment of Periodic Limb Movements in Sleep with Selegine HCl," Movement Disorders 17 (2) : 398-401.
Hening, W.A., (2004) "An Update on the Dopaminergic Treatment of Restless Legs Syndrome and Periodic Limb Movement Disorder", Sleep, vol. 27, No. 3, p. 560-583.
Hubalek et al. "inactivation of Purified Human Recombinant Monoamine Oxidases A and B by Rasagiline and Its Analogues", Journal of Medicinal Chemistry, 2004, vol. 47, pp. 1760-1766.
Jones et al., Restless Legs Syndrome—A Review, Eur.J.Vasc. Endovasc.Surg., Dec. 1997, 14 (6) :430-2.
J. Mendlewicz and M.B.H. Youdim, Brit. J. Psychiat., 1983, 142, 508-511.
Kalir, et al., "Selective Acetylenic 'Suicide' and Reversible Inhibitors of Monoamine Oxidase Types A and B"; British Journal of Pharmacology, vol. 73, 55064 (1981).
The Merck Manual, 17th Ed. 1999, 1416.
Montplaisir J. et al., Restless Legs Syndrome and Periodic Movements in Sleep: Physiopathology and Treatment with L-dopa, Clin. Neuropharmacol., 1986, 9 (5) :456-463.
Montplaisir et al. Eur. J. Neurol., vol. 13, No. 12, pp. 1306-1311 (2006) (Abstract Only).
Northwest Behavioral Medicine, www.psychatlanta.com/documents/maoi.pdf, Monoamine Oxidase Inhibitors, Apr. 2007, pp. 1-6.
Ondo, W. et al. "Clinical correlates of 6-hydroxydopamine injections into All dopaminergic neurons in rats: A possible model for restless legs syndrome?" Movement disorders, vol. 15, No. 1, Jan. 1, 2000, pp. 154-158.
Research News, Gene and Protein, Nov. 2002, p. 1.
Restless Leg Syndrome Foundation, Inc. Medical Bulletin, Apr. 2004, p. 15.
Silber M.H. et al., Pergolide in the Management of Restless Legs Syndrome: An Extended Study, Sleep, 1997, 20 (10) :878-882.
Telstad W. et al., Treatment of the Restless Legs Syndrome with Carbamazepine; A Double Blind Study, Br. Med. J. (Clin.Res. Ed.) , 1984, 288 (6415) :444-446.

(56) References Cited

OTHER PUBLICATIONS

Thorpy J. Michael. New Paradignms in the treatment of restless legs syndrome. Neurology 2005; 64: S28-S33.
Walters, A.S. et al., Successful Treatment of the Idiopathic Restless Legs Syndrome in a Randomized Double-Blind Trial of Oxycodone Versus Placebo, Sleep, 1993, 16 (4) :327-332.
Youdim et al., Progress in Medicinal Chemistry, 1984, 21, 138-167.
Youdim et al. in Handbook of Experimental Pharmacology vol. 90/I (1988) Chapter 3, Trendlenburg and Weiner, eds.
Youdim MBH, et al., "Rasagiline (N-propargyl-1R (+)-aminoindan) , a selective and potent inhibitor of mitochondrial monoamine oxidase B", Br. J. Pharmacol., 2001,132:500-6.

\* cited by examiner

USE OF RASAGILINE FOR THE TREATMENT OF RESTLESS LEGS SYNDROME This application is a continuation of U.S. Ser. No. 17/306,106, filed May 3, 2021, a continuation of U.S. Ser. No. 17/152,514, filed Jan. 19, 2021, a continuation of U.S. Ser. No. 17/065,811, filed Oct. 8, 2020, a continuation of U.S. Ser. No. 16/913,633, filed Jun. 26, 2020, a continuation of U.S. Ser. No. 16/815,979, filed Mar. 11, 2020, a continuation of U.S. Ser. No. 16/696,568, filed Nov. 26, 2019, a continuation of U.S. Ser. No. 16/543,164, filed Aug. 16, 2019, a continuation of U.S. Ser. No. 16/405,468, filed May 7, 2019, a continuation of U.S. Ser. No. 16,233,046, filed Dec. 26, 2018, a continuation of U.S. Ser. No. 16/102,148, filed Aug. 13, 2018, a continuation of U.S. Ser. No. 15/895,962, filed Feb. 13, 2018, a continuation of U.S. Ser. No. 15/697,935, filed Sep. 7, 2017, a continuation of U.S. Ser. No. 15/096,038, filed Apr. 11, 2016, a continuation of U.S. Ser. No. 14/524,993, filed Oct. 27, 2014, a continuation of U.S. Ser. No. 11/731,493, filed Mar. 30, 2007, which claims the benefit of U.S. Provisional Application No. 60/788,617 filed Apr. 3, 2006, the entire contents of each of which in their entireties are hereby incorporated by reference.

Throughout this application various publications, published patent applications and published patents are referenced. The disclosures of these publications in their entireties are hereby incorporated by reference into this application in order to more fully describe the state of the art to which this invention pertains.

BACKGROUND OF THE INVENTION

Restless Legs Syndrome ("RLS", also known as Ekbom Syndrome) is a neurological condition that expresses itself as an overwhelming urge to move the legs, usually caused by uncomfortable or unpleasant sensations in the legs at rest. Movement of the legs temporarily alleviates the discomfort. (Jones et al., Restless Legs Syndrome—A Review, *Eur. J. Vasc. Endovasc. Surg.*, December 1997, 14(6):430-2)

The sensations occur during periods of inactivity, and are thus most intense in the evening and at night. RLS often causes difficulty staying or falling asleep, which leads to feelings of daytime tiredness or fatigue. RLS may cause involuntary jerking of the limbs during sleep and sometimes during wakefulness. Because of the nature of these symptoms, RLS is one of the most prevalent causes of sleep disorders such as sleep disturbance and insomnia. (Fox, G. N., Restless Legs Syndrome, *American Family Physician*, January 1986, 33(1):147-52)

RLS can occur at any age but increases in frequency as persons grow older. (Thorpy J. Michael. New Paradignms in the treatment of restless legs syndrome. Neurology 2005; 64: S28-S33) It afflicts about 8% of the general population. (see, rls.org/)

At least 80% of RLS patients experience periodic leg movements (PLMs), stereotyped, repetitive flexion movements of the legs that occur approximately every 5-90 seconds when the patient is asleep or lying down resting. (Hening A Wayne et al. An update on the dopaminergic treatment of restless legs syndrome and periodic limb movement disorder. Sleep 2004, 27: 560-583.) Both the sensations in the limbs and the PLMs can profoundly disrupt sleep (getting to sleep and staying asleep). This can lead to excessive daytime sleepiness as well as depression and anxiety and may have a significant negative impact on quality of life.

Treatment of RLS can be difficult and often requires trying different drugs and dosage regimes. (*The Merck Manual*, 17th Ed. 1999, 1416) The primary pharmacologic treatment of RLS is principally with two classes of medications: dopaminergic agents and opiate agents. (Restless Legs Syndrome Foundation, Inc. Medical Bulletin, April 2004, pg. 15)

Nearly all patients with RLS show at least an initial positive therapeutic response to dopamine precursor levodopa (L-dopa) (either alone or with a dopa decarboxylase inhibitor like carbidopa) at dosages very low compared with those prescribed in the treatment of Parkinson's disease. (Montplaisir J. et al., Restless Legs Syndrome and Periodic Movements in Sleep: Physiopathology and Treatment with L-dopa, *Clin. Neuropharmacol.*, 1986, 9(5):456-463) This initial response, however, is not universally maintained. The drawback of L-dopa therapy lies in the fact that in many patients its effectiveness tapers off and/or the RLS problem is shifted toward the morning hours (rebound) or the disorder is aggravated with the problem occurring event during the day (augmentation). (Guilleminault C. et al., Dopaminergic Treatment of Restless Legs and Rebound Phenomenon, *Neurology*, 1993, 43(2):445; and Allen R. P., Augmentation of the Restless Legs Syndrome with Carbidopa/Levodopa, *Sleep*, 1996, 19(3):205-213)

Dopamine-receptor agonists such as pergolide and pramipexole, known by the trade name Mirapex [available from Boehringer Ingelheim Pharmaceuticals, Inc., Ridgefield, CT], provide well-established and effective treatment for RLS. However, they have been reported to cause major side effects. (Dooley M. et al., Pramipexole: A Review of Its Use in the Management of Early and Advanced Parkinson's Disease, *Drugs Aging*, June 1998, 12(6):495-514; and Silber M. H. et al., Pergolide in the Management of Restless Legs Syndrome: An Extended Study, *Sleep*, 1997, 20(10):878-882) In fact, all of the dopamine agonists can be used to treat RLS but with a negative aspect in that, usually in the beginning and as a function of the dosage administered, they lead to such side effects as nausea, vomiting, dizziness, hypotension, constipation or insomnia. (Medical Bulletin, infra at pg. 17)

Opiates are effective against RLS as well, although often at relatively high doses. (Walters, A. S. et al., Successful Treatment of the Idiopathic Restless Legs Syndrome in a Randomized Double-Blind Trial of Oxycodone Versus Placebo, *Sleep*, 1993, 16(4):327-332) However, because of the risk of addiction and progressive tolerance these substances are suitable for therapeutic application to a limited extent at best.

Benzodiazepines such as clonazepam and anticonvulsants such as gabapentin and carbamazepine have also been shown to alleviate the symptoms of RLS. (Medical Bulletin, infra at pg. 19) However, side effects similar to those associated with the treatments described above limit use. Addiction and daytime sedation are problematic with benzodiapenes, which does not prevent movement but only prevents awakening. (Id.) High dosages are required in anticonvulsant treatments. Furthermore, it is thought that anticonvulsants fail to resolve the full spectrum of elements of RLS. (Telstad W. et al., Treatment of the Restless Legs Syndrome with Carbamazepine; A Double Blind Study, *Br. Med. J. (Clin. Res. Ed.)*, 1984, 288(6415):444-446)

Valproate has also shown benefit for RLS, but the side effect of weight gain has limited its acceptance. (Dinesin H. et al., Weight Gain During Treatment With Valproate, *Acta. Neurol. Scan.*, 1984, 70(2):65-69)

Clonidine, originally developed as an antihypertensive agent and miotic, has also been examined for its effectiveness in the treatment of RLS. While it was found that soporiferous latency was reduced, it had no effect on the quality of sleep, the frequency of waking up or periodic leg movement during sleep. Given that more efficacious substances are available for monotherapy, clonidine is not currently recommended as an alternative form of therapy except in limited situations. (U.S. Patent Publication No. 2001/0053777, published Dec. 20, 2001)

Therefore, there exists a need for an effective, alternative treatment and related treatment regime options for individuals who are afflicted with RLS. More particularly, there exists a need for treatments that do not induce the unwanted effects observed in modern therapeutics of RLS.

SUMMARY OF THE INVENTION

This subject invention provides a method of treating a subject suffering from Restless Legs Syndrome which comprises administering to the subject an amount of R(+)-N-propargyl-1-aminoindan or a pharmaceutically acceptably salt thereof, effective to treat the subject.

The subject invention also provides a method of alleviating a symptom of Restless Legs Syndrome in a subject afflicted with Restless Legs Syndrome comprising administering to the subject an amount of R(+)-N-propargyl-1-aminoindan or a pharmaceutically acceptable salt thereof effective to alleviate the symptom of Restless Legs Syndrome in the subject.

The subject invention also provides a pharmaceutical composition comprising in unit dosage form R(+)-N-propargyl-1-aminoindan or a pharmaceutically acceptable salt thereof and at least one of pergolide, pramipexole, oxycodone, clonazepam, carbamazepine, gabapentin, valproate, ropinirole or clonidin.

The subject invention also provides a pharmaceutical composition for use in the treatment of, or alleviation of symptoms of, Restless Legs Syndrome, which comprises a therapeutically effective amount of R(+)-N-propargyl-1-aminoindan or a pharmaceutically acceptable salt thereof and a pharmaceutically acceptable carrier.

The subject invention also provides use of R(+)-N-propargyl-1-aminoindan or a pharmaceutically acceptable salt thereof in the manufacture of a medicament for the treatment of, or alleviation of symptoms of, Restless Legs Syndrome.

The subject invention also provides a pharmaceutical composition comprising in unit dosage form R(+)-N-propargyl-1-aminoindan or a pharmaceutically acceptable salt thereof and pramipexole.

DETAILED DESCRIPTION

The subject invention provides a method of treating a subject suffering from Restless Legs Syndrome which comprises administering to the subject an amount of R(+)-N-propargyl-1-aminoindan or a pharmaceutically acceptably salt thereof, effective to treat the subject.

The subject invention also provides a method of alleviating a symptom of Restless Legs Syndrome in a subject afflicted with Restless Legs Syndrome comprising administering to the subject an amount of R(+)-N-propargyl-1-aminoindan or a pharmaceutically acceptable salt thereof effective to alleviate the symptom of Restless Legs Syndrome in the subject.

In an embodiment, the symptom may be any of tingling in the legs, cramps in the legs, pain in the legs or restlessness in the legs.

In the methods, the IRLS Rating Scale score of the subject decreases compared to the baseline.

In an embodiment of the methods, the decrease is a 20% decrease, preferably a 30% decrease, more preferably a 40% decrease, yet more preferably a 50% decrease of the IRLS Rating Scale Score.

In an embodiment, the amount of R(+)-N-propargyl-1-aminoindan or of the pharmaceutically acceptable salt thereof may be from 0.01 mg to 20 mg per day. By 0.01 mg to 20 mg it is meant that all hundredth, tenth and integer unit amounts within the range are specifically disclosed as part of the invention. Thus, 0.02, 0.03 . . . 0.09; 0.1, 0.2 . . . 0.9; 1, 2 . . . 19 mg unit amounts are included as embodiments of this invention.

In a further embodiment, the therapeutically effective amount of R(+)-N-propargyl-1-aminoindan or of the pharmaceutically acceptable salt thereof may be from 0.5 mg to 5 mg per day.

In a specific embodiment, the amount may be 1.0 mg. By 0.5 mg to 5 mg it is meant that all tenth and integer unit amounts within the range are specifically disclosed as part of the invention. Thus, 0.6, 0.7 . . . 0.9; 1, 2 . . . 4 mg unit amounts are included as embodiments of this invention.

In an embodiment, a dose of R(+)-N-propargyl-1-aminoindan or of the pharmaceutically acceptable salt thereof may be administered 1 to 4 times a day.

In a further embodiment, a dose of R(+)-N-propargyl-1-aminoindan or of the pharmaceutically acceptable salt thereof may be administered once a day.

Furthermore, an evening dose of R(+)-N-propargyl-1-aminoindan or of the pharmaceutically acceptable salt thereof may be administered to a subject 1 to 3 hours before the subject goes to bed.

Yet furthermore, a second dose is administered to the subject 3 to 7 hours before the evening dose.

In another embodiment, a dose of R(+)-N-propargyl-1-aminoindan or of the pharmaceutically acceptable salt thereof is administered to the subject at 3 to 7 hour intervals throughout the day.

In an embodiment, the administration is of R(+)-N-propargyl-1-aminoindan.

In a further embodiment, the administration is of the pharmaceutically acceptable salt of R(+)-N-propargyl-1-aminoindan.

The pharmaceutically acceptable salt of the methods may be esylate, mesylate, sulfate or tartrate.

In a specific embodiment, the pharmaceutically acceptable salt may be mesylate.

In a further embodiment, the therapeutically effective amount of R(+)-N-propargyl-1-aminoindan mesylate may be 1.66 mg per day.

1 mg of the base compound R(+)-N-propargyl-1-aminoindan amounts to 1.66 mg of R(+)-N-propargyl-1-aminoindan mesylate.

In an embodiment, the administration may be oral, parenteral, rectal or transdermal administration.

In a further embodiment of the invention, the methods further comprise administration of carbidopa, levodopa, pergolide, pramipexole, oxycodone, clonazepam, carbamazepine, gabapentin, valproate, ropinirole or clonidin.

In an embodiment, the administration of R(+)-N-propargyl-1-aminoindan or the salt substantially precedes the administration of any of carbidopa, levodopa, pergolide, pramipexole, oxycodone, clonazepam, carbamazepine, gabapentin, valproate, ropinirole or clonidin.

In a further embodiment, the administration of R(+)-N-propargyl-1-aminoindan or the salt is contemporaneous with the administration of any of carbidopa, levodopa, pergolide, pramipexole, oxycodone, clonazepam, carbamazepine, gabapentin, valproate, ropinirole or clonidin.

The R(+)-N-propargyl-1-aminoindan or the pharmaceutically acceptable salt thereof may be in a pharmaceutical composition when used in the methods.

In an embodiment, the pharmaceutical composition is in tablet form.

In an embodiment, the pharmaceutical composition is in a form suitable for transdermal administration.

In an embodiment, the pharmaceutical composition is in a form suitable for sublingual administration.

The subject invention also provides a pharmaceutical composition comprising in unit dosage form R(+)-N-propargyl-1-aminoindan or a pharmaceutically acceptable salt thereof and at least one of pergolide, pramipexole, oxycodone, clonazepam, carbamazepine, gabapentin, valproate, ropinirole or clonidin.

The subject invention also provides a pharmaceutical composition comprising in unit dosage form R(+)-N-propargyl-1-aminoindan or a pharmaceutically acceptable salt thereof and pramipexole.

In an embodiment, the amount of R(+)-N-propargyl-1-aminoindan or of the pharmaceutically acceptable salt thereof is from 0.5 mg to 5 mg.

In a further embodiment, the amount of R(+)-N-propargyl-1-aminoindan is 1 mg.

In a further embodiment, the R(+)-N-propargyl-1-aminoindan is the pharmaceutically acceptable salt of R(+)-N-propargyl-1-aminoindan.

In a further embodiment, the pharmaceutically acceptable salt is esylate, mesylate, sulfate or tartrate.

In a further embodiment, the pharmaceutically acceptable salt is mesylate.

In a further embodiment, the amount of R(+)-N-propargyl-1-aminoindan mesylate is 1.66 mg.

In a further embodiment, the amount of pramipexole is from 0.125 mg to 0.6 mg.

In a further embodiment, the amount of pramipexole is from 0.375 mg to 6.0 mg.

In a further embodiment, the amount of pramipexole is 0.6 mg.

In a further embodiment, the pramipexole is in a pharmaceutically acceptable salt form.

In a further embodiment, the pharmaceutically acceptable salt form is pramipexole dihydrochloride.

In a further embodiment, the amount of pramipexole dihydrochloride is 0.6 mg.

In a further embodiment, the amount of pramipexole dihydrochloride is 0.75 mg.

In a further embodiment, the amount of pramipexole is from 0.125 mg to 0.6 mg.

In a further embodiment, the amount of pramipexole is from 0.375 mg to 6.0 mg.

In a further embodiment, the amount of pramipexole is 0.6 mg.

In a further embodiment, the pramipexole is in a pharmaceutically acceptable salt form.

In a further embodiment, the pharmaceutically acceptable salt form is pramipexole dihydrochloride.

In a further embodiment, the amount of pramipexole dihydrochloride is 0.6 mg.

In a further embodiment, the amount of pramipexole dihydrochloride is 0.75 mg.

The subject invention also provides a pharmaceutical composition for use in the treatment of, or alleviation of symptoms of, Restless Legs Syndrome, which comprises a therapeutically effective amount of R(+)-N-propargyl-1-aminoindan or a pharmaceutically acceptable salt thereof and a pharmaceutically acceptable carrier.

The subject invention also provides use of R(+)-N-propargyl-1-aminoindan or a pharmaceutically acceptable salt thereof in the manufacture of a medicament for the treatment of, or alleviation of symptoms of, Restless Legs Syndrome. Such use can have the same embodiments as those specifically disclosed herein in the context of a method.

The present invention thus provides the R-(+)-enantiomer of N-propargyl-1-aminoindan ["R(+)PAI"] of the formula (I):

and pharmaceutically acceptable acid additions salts thereof for the treatment of human patients for Restless Legs Syndrome ("RLS"). The present invention also provides pharmaceutical compositions comprising the compound R(+)PAI, their preparations and methods of treatment of RLS with the pharmaceutical compositions.

The subject invention also provides a method for the treatment of RLS with rasagiline, wherein, the patient has previously been diagnosed and treated for RLS and developed symptoms of augmentation, i.e. a common consequence of long term treatment in which the symptoms of RLS become more severe, occur earlier in the evening, and spread to other parts of the body.

Rasagiline is the INN (International Nonproprietary Name) and USAN (United States Adopted Name) of the chemical substance R-(+)-N-propargyl-1-aminoindan.

R(+)PAI may be obtained by optical resolution of racemic mixtures of R and S-enantiomer of N-propargyl-1-aminoindan (PAI). Such a resolution can be accomplished by any conventional resolution method, well known to a person skilled in the art, such as those described in "Enantiomers, Racemates and Resolutions" by J. Jacques, A. Collet and S. Wilen, Pub. John Wiley & Sons, N.Y., 1981. For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallisation to isolate the diastereomeric salt of the desired R enantiomer.

The racemic mixture of R and S enantiomers of PAI may be prepared, e.g. as described in WO95/11016. The racemic mixture of PAI can also be prepared by reacting 1-chloroindan or 1-bromoindan with propargylamine. Alternatively, this racemate may be prepared by reacting propargylamine with 1-indanone to form the corresponding imine, followed by reduction of the carbon-nitrogen double bond of the imine with a suitable agent, such as sodium borohydride.

In accordance with this invention, R(+)PAI can also be prepared directly from the optically active R-enantiomer of 1-aminoindan by reaction with propargyl bromide or propargyl chloride in the presence of an organic or inorganic base and optionally in the presence of a suitable solvent. A preferred method of preparation of the aforementioned compound is the reaction between R-1-aminoindan with propargyl chloride using potassium bicarbonate as a base and acetonitrile as solvent.

The compound R(+)PAI may be prepared as pharmaceutical compositions particularly useful for the treatment of RLS. Such compositions may comprise the compound of R(+)PAI or pharmaceutically acceptable acid addition salts thereof, together with pharmaceutically acceptable carriers and/or excipients. In the practice of this invention, pharmaceutically acceptable salts include, but are not limited to, the mesylate, maleate, fumarate, tartrate, hydrochloride, hydrobromide, esylate, p-tolunesulfonate, benzoate, acetate, phosphate and sulfate salts.

The compound pramipexole is a non-ergoline dopamine agonist effective as an adjunct therapy to levodopa in the treatment of patients with advanced Parkinson's disease experiencing motor effects. It is also effective as a monotherapy in early Parkinson's disease patients where it has shown improvement in daily living and motor symptoms. Pramipexole has been determined to act at dopamine D2 receptors, specifically at presynaptic dopamine D2 autoreceptors and postsynaptic dopamine D2 receptors. (Dooley M. et al., Pramipexole: A Review of Its Use in the Management of Early and Advanced Parkinson's Disease, *Drugs Aging*, June 1998, 12(6):495-514.

Pramipexole may be administered from 0.375 to 6.0 mg/day and in unit dosage from 0.125 to 1.5 mg. Pramipexole may be administered orally, inraperitoneally, subcutaneously or intravenously. (Dooley M. et al., Pramipexole: A Review of Its Use in the Management of Early and Advanced Parkinson's Disease, *Drugs Aging*, June 1998, 12(6):495-514.

Pramipexole may be in the form of pramipexole base. In the practice of this invention, a pharmaceutically acceptable salt form of pramipexole includes pramipexole dihydrochloride. (Dooley M. et al., Pramipexole: A Review of Its Use in the Management of Early and Advanced Parkinson's Disease, *Drugs Aging*, June 1998, 12(6):495-514.

Pramipexole may be initially administered at a dosage which is gradually increased until symptoms are relieved. (Dooley M. et al., Pramipexole: A Review of Its Use in the Management of Early and Advanced Parkinson's Disease, *Drugs Aging*, June 1998, 12(6):495-514.

Pramipexole may be administered 3 times daily. (Dooley M. et al., Pramipexole: A Review of Its Use in the Management of Early and Advanced Parkinson's Disease, *Drugs Aging*, June 1998, 12(6):495-514.

The compositions may be prepared as medicaments to be administered orally, parenterally, rectally or transdermally. Suitable forms for oral administration include tablets, compressed or coated pills, dragees, sachets, hard or soft gelatin capsules, sublingual tablets, syrups and suspensions; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art.

Specific examples of pharmaceutical acceptable carriers and excipients that may be used to formulate oral dosage forms of the present invention are described, e.g., in U.S. Pat. No. 6,126,968 to Peskin et al., issued Oct. 3, 2000.

Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences Vol 40 (Gilbert S. Banker, Christopher T. Rhodes, Eds.).

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Rasagiline mesylate in a 1 mg tablet is commercially available for use in Parkinson's disease treatment as Azilect® from Teva Pharmaceutical Industries, Ltd. (Petach Tikva, Israel) and H. Lundbeck A/S (Copenhagen, Denmark). See, also AZILECT®, Physician's Desk Reference (2006), 60$^{th}$ Edition, Thomson Healthcare. The cognitive and behavioral adverse events of hallucinations, confusion, depression, somnolence and other sleep disorders in subjects treated with Azilect® are few and do not exceed the incidence seen in subjects receiving placebo by more than 3 percent. (Parkinson Study Group, Tyramine Challenge to Assess the Safety of Rasagiline Monotherapy in a Placebo-Controlled Multicenter Trial for Early Parkinson's Disease (The TEMPO Study), *Neurology*, 2001, 56:A345) The most commonly reported adverse events in rasagiline-treated subjects are pain, headache and dizziness. Side effects typically associated with other dopaminergic medications, such as hallucinations, somnolence, edema, nausea, vomiting, and diarrhea, are infrequently reported in rasagiline-treated subjects. (Stern et al., Double-Blind, Randomized, Controlled Trial of Rasagiline as Monotherapy in Early Parkinson's Disease Patients, *Mov. Disord.,* 2004, 19(8):916-923)

R(+)PAI compositions may be used alone to treat RLS, or alternatively, they may be used as an adjunct to existing RLS treatments. R(+)PAI may be administered at different times and separate from other RLS treatments, or as a combined pharmaceutical composition of R(+)PAI with at least one of carbidopa, levodopa, pergolide, pramipexole, oxycodone, clonazepam, carbamazepine, gabapentin, valproate, ropinirole or clonidin. Thus, for example, a pharmaceutical composition for oral use in the form of tablets or capsules may comprise R(+)-N-propargyl-1-aminoindan, Levodopa, and a decarboxylase inhibitor. Such a composition may comprise 0.01-20 mg of R(+)-N-propargyl-1-aminoindan, 50-100 mg of Levodopa, and 12.5-50 mg of benserazide.

The preferred dosages of R(+)PAI in any of the disclosed compositions may be within the following ranges: for oral or suppository formulations 0.01-20 mg per dosage unit to be taken daily and more preferably 0.5-5 mg per dosage unit to be taken daily may be used; and for injectable formulations 0.05-10 mg/ml per dosage unit to be taken daily and more preferably 0.5-3 mg/ml per dosage unit to be taken daily may be used.

By 0.01-20 mg it is meant that all hundredth, tenth and integer unit amounts within the range are specifically disclosed as part of the invention. Thus, 0.02, 0.03 . . . 0.09; 0.1, 0.2 . . . 0.9; and 1, 2 . . . 19 mg unit amounts are included as embodiments of this invention.

R(+)PAI is effective and suitable for use in the treatment of RLS, both alone and in combination with other RLS treatments.

Furthermore, unlike several known treatments of RLS, the use of rasagiline as the active ingredient for treating RLS improves the subject's condition without causing undesirable side effects. The subject is a human subject.

EXPERIMENTAL DETAILS

Example 1

| | |
|---|---|
| R(+)-N-propargyl-1-aminoindan mesylate | 3.12 mg/tablet |
| Mannitol | 62.5 mg/tablet |
| Maltodextrin (Maltrin 150) | 36.0 mg/tablet |
| Croscarmellose sodium (Ac-Di-Sol) | 2.1 mg/tablet |
| Talc | 1.5 mg/tablet |

Example 2

| | |
|---|---|
| RW-N-propargyl-1-aminoindan mesylate | 1.56 mg/tablet |
| Mannitol | 79.14 mg/tablet |
| Starch | 10.0 mg/tablet |
| Pregelatinized starch | 10.0 mg/tablet |
| Colloidal silicon dioxide | 0.6 mg/tablet |
| Talc | 2.0 mg/tablet |
| Stearic acid | 2.0 mg/tablet |

Example 3

| | |
|---|---|
| R(+)-N-propargyl-1-aminoindan mesylate | 3.12 mg/tablet |
| Mannitol | 76.58 mg/tablet |
| Starch | 10.0 mg/tablet |
| Pregelatinized starch | 10.0 mg/tablet |
| Colloidal silicon dioxide | 0.6 mg/tablet |
| Citric acid | 1.0 mg/tablet |
| Talc | 2.0 mg/tablet |

Example 4

| | |
|---|---|
| R(+)-N-propargyl-1-aminoindan mesylate | 3.12 mg/tablet |
| Mannitol | 69.88 mg/tablet |
| Lactose (hydrous) | 14.0 mg/tablet |
| Starch | 14.0 mg/tablet |
| Glyceryl Behenate (Compitrol 888 ATO) | 2.0 mg/tablet |

Example 5

| | |
|---|---|
| R(+)-N-propargyl-1-aminoindan mesylate | 3.12 mg/tablet |
| Mannitol | 77.28 mg/tablet |
| Starch | 10.0 mg/tablet |
| Starch STA-RX 1500 | 10.0 mg/tablet |
| Colloidal silicon dioxide, Aerosil | 0.6 mg/tablet |
| Hydrogenated vegetable type I (Sterotex Dritex) | 2.0 mg/tablet |

Example 6—Rat Model of RLS 6-hydroxydopamine is an agent that selectively disrupts or destroys catecholaminergic systems. Thus, stereotaxic bilateral 6-hydroxydopamine lesions into the nucleus of dopaminergic diencephalic spinal neurons (A11) are performed to effect behavior consistent, although not specific, with what would be expected in a rat model of RLS. (Ondo W. G. et al., Clinical Correlates of 6-Hydroxydopamine Injections into A11 Dopaminergic Neurons in Rats: A Possible Model for Restless Leg Syndrome, *Mov. Disord.*, 2000, 15(1):154-8)

Multiple blindly-rated video epochs demonstrate an increased average number of standing episodes and increased total standing time but similar total sleep time in lesioned rats when compared with control rats. However, treatment of the lesioned rats with R(+)PAI mesylate results in fewer standing episodes and less total standing time when compared with untreated lesioned rats.

Example 7—RLS Model Spontaneously Occurring During Sleep of Rats

Periodic limb movements in sleep (PLMS) are often associated with RLS. In a group of old rats 16-20 months, sleep-wake behavior is recorded and hindlimb movements are detected by means of a magneto-inductive device during two 12-h light periods (Baier P. C. et al., Assessment of spontaneously occurring periodic limb movements in sleep in the rat, J. Neurol. Sci. 2002; 198(1-2): 71-77). Periodic hindlimb movements (PHLM) during nonrapid eye movement sleep (NREM) are identified according to modified human criteria in some of the rats, which are then selected for the rasagiline study. Half the rats are treated daily with rasagiline while the other half receive vehicle. Incidence of PHLM is determined for 3 consecutive nights, beginning 7 days after onset of treatment. It is demonstrated that rasagiline-treated rats have significantly fewer PHLM than vehicle-treated rats.

Example 8

The 1 mg tablet of R(+)PAI mesylate is investigated in placebo-controlled, double-blind, randomized clinical tests covering in a study adult patients who are suffering from moderate to severe primary Restless Legs Syndrome.

Randomization in terms of gender, age and severity of prior illnesses is reasonably balanced. Patients with RLS secondary to other conditions (e.g., pregnancy, renal failure, and anemia) are excluded.

After gradual and complete termination of any preceding L-dopa treatment and a break in the therapy (washout) the patients are treated with R(+)PAI.

Over a treatment period of days the patients of one group are treated with a 0.5 mg dosage and the patients of another group are treated with 1 mg. For a comparison the patients in the placebo group are treated with a placebo.

Severity of symptoms is measured with a rating scale developed by the International Restless Legs Syndrome Study Group ("IRLSSG") (http://www.irlssg.org/). Use of the scale is common for clinical assessment, research and therapeutic trials with RLS. The overall IRLSSG rating is derived from the individual values discussed below.

First, an initial starting value is determined for each patient participating in the study. This is done by adding up the individual IRLSSG parameter values as of Day 0, i.e. before treatment. Over the course of treatment the IRLSSG values are compared with the starting value and any changes from that starting value are recorded. Finally, the average improvement of the IRLSSG value over the starting value is determined by calculating the average of all test subjects. The resulting value is called CAS—(complete analysis set) randomized average change from the starting value of the overall IRLSSG rating. The term "randomized" indicates that in terms of their different prespecified dosages the patients are subjected to prior double-blind randomization.

Results

Between the starting value and that established after treatment, a significant improvement of the IRLSSG values is recorded in comparison with the placebo group.

At the end of the treatment both patient groups report that subjective symptoms such as tingling, cramps and pain in the legs, restlessness in the legs during the night, and difficulties falling or remaining asleep either disappear or diminish to a tolerable minimum.

The patients also report that the treatment does not or only to a very minimal extent causes any hallucinations, somnolence, edema, nausea, vomiting or diarrhea.

Accordingly, R(+)PAI is well tolerated and safe and leads to a distinct clinical improvement in patients in a moderate to severe stage of RLS.

An improvement of the IRLSSG value of 2 points compared to a placebo can be considered a success. An improvement by over 3 or 6 and more rating units constitutes an all the more significant therapeutic advance and is therefore the preferred objective of this invention.

Example 9

This was the first clinical study in which rasagiline was administered to RLS subjects. The dosage regimen of 1 mg/day rasagiline was chosen based on the optimal dosage regimen for the symptomatic treatment of PD. However, smaller doses than those required for the treatment of PD are expected to be efficacious in the treatment of RLS. Therefore, in the event that a subject could not tolerate the 1 mg daily dose of rasagiline, a daily dose of 0.5 mg rasagiline was permitted. Rasagiline was administered orally as a tablet. Both the 1 mg and 0.5 mg rasagiline tablets were beveled round tablets, flat, white to off-white, scored on one side, plain on the other side. Teva Pharmaceutical Industries Ltd. was responsible for the manufacture and primary packaging of study medications according to current Good Manufacturing Practice (cGMP) principles and guidelines applicable to investigational medicinal products.

| Visit Week No. | Week-$2^a$ (screening) | Week 0 (baseline) | Week 2 ±4 | Week 4 ±4 | Week 8 ±4 | Week 12/ Early Termination ±4 | Unscheduled Visit$^b$ |
|---|---|---|---|---|---|---|---|
| Informed consent | X | | | | | | |
| Inclusion/ Exclusion criteria | X | X | | | | | |
| Medical history | X | | | | | | |
| Concomitant medications | X | X | X | X | X | X | X |
| IRLS | X | X | X | X | X | X | |
| Sleep Scale | | X | | X | X | X | |
| CGI-I | | | X | X | X | X | |
| RLS Quality of Life Questionnaire | | X | | X | X | X | |
| Adverse events | | X | X | X | X | X | X |
| AE follow lip | | | | | | X | |
| Laboratory test including β-hCG$^c$ | X | | | | | X | X |
| Vital signs$^d$ | X | X | X | X | X | X | X |
| ECG | X | | | | | X | X |
| Dermatological evaluation | X | | | | | X | X |
| Study termination | | | | | | X | |
| Retrieve study drug and assess compliance | | | X | X | X | X | X |
| Dispense study drug | | X | X | X | X | | X |

$^a$) The maximal interval between the screening and baseline visits should be 14 days. If, however, results from screening procedures are still pending after 14 days from the screening visit and the investigator has to wait until all results are available before determining a subject's eligibility, the interval between the screening and baseline visits may extend up to 21 days.
$^b$) Procedures during an unscheduled visit are optional, except vital signs.
$^c$) Pregnancy test relevant to women of childbearing potential only
$^d$) Including weight and height at screening and weight at Visit Week 8/Early Termination IRLS (International Restless Legs Scale)

The IRLS scale is comprised of 10 items designed to assess the severity of sensory and motor symptoms, sleep disturbance, daytime somnolence, and impact on activities of daily living and mood associated with RLS. All items receive a grade in the range 0 to 4 (0=absence of a problem, 4=very severe problem) giving a maximum score of 40.

The investigator scored subjects on the IRLS at all scheduled study visits. The primary efficacy endpoint was based on the change from baseline to weeks 2, 4, and 8 in IRLS scores.

IRLS Scale

Each of 10 items were graded on a scale between 0 and 4 where 0 denotes the absence of a problem, and 4 a very severe problem. Table 1 shows the results; a low score indicates the absence of a problem and a high score indicates a very severe problem.

TABLE 1

Descriptive Statistics of IRLS Rating Scale and Change from Baseline Over Time

| | IRLS Total | | | | | | IRLS Total (Absolute Change) | | | | | | IRLS Total (Percent Change) | | | | |
|---|---|---|---|---|---|---|---|---|---|---|---|---|---|---|---|---|---|
| Week | N | Mean | SD | Min | Median | Max | N | Mean | SD | Min | Median | Max | N | Mean | SD | Min | Median | Max |
| BASELINE | 2 | 32.00 | 8.49 | 26.00 | 32.00 | 38.00 | 2 | 0.00 | 0.00 | 0.00 | 0.00 | 0.00 | 2 | 0.00 | 0.00 | 0.00 | 0.00 | 0.00 |
| VISIT WEEK 1 | 2 | 29.00 | 12.73 | 20.00 | 29.00 | 38.00 | 2 | −3.00 | 4.24 | −6.00 | −3.00 | 0.00 | 2 | −11.54 | 16.32 | −23.08 | −11.54 | 0.00 |
| VISIT WEEK 4 | 2 | 25.50 | 17.68 | 13.00 | 25.50 | 38.00 | 2 | −6.50 | 9.19 | −13.00 | −6.50 | 0.00 | 2 | −25.00 | 35.36 | −50.00 | −25.10 | 0.00 |
| VISIT WEEK 3 | 1 | 12.00 | | 12.00 | 12.00 | 12.00 | 1 | −14.00 | | −14.00 | −14.00 | −14.00 | 1 | −53.85 | | −53.85 | −53.85 | −53.85 |

Clinical Global Impression-Global Improvement (CGI-I)

The CGI-I scale is a single item scale on which the investigator rated a subject's symptoms as very much improved, much improved, minimally improved, not changed, minimally worse, much worse, or very much worse. Subjects were scored on this scale at weeks 2, 4, and 8. The mean score at each of these time points was calculated as a secondary efficacy endpoint. Table 2 shows the results of the CGI-I Rating Scale. Subjects are scored on a scale of 1-7, where 1 indicates the subject's symptoms are very much improved and 7 indicates the subject's symptoms are very much worse.

TABLE 2

Descriptive Statistics of CGI-I Rating Scale

| | CGI-I Total | | | | | |
|---|---|---|---|---|---|---|
| Week | N | Mean | SD | Min | Median | Max |
| VISIT WEEK 2 | 2 | 3.50 | 0.71 | 3.00 | 3.0 | 4.00 |
| VISIT WEEK 4 | 2 | 3.50 | 2.12 | 2.00 | 3.50 | 5.00 |
| VISIT WEEK 8 | 1 | 1.00 | | 1.00 | 4.00 | 1.00 |

RLS QoL Questionnaire

The Restless Leg Syndrome Quality of Life questionnaire (RLS QoL) assesses the impact of RLS on daily life, emotional well-being, social life and work life. It is an 18-item questionnaire with a total score ranging 0 to 100. Table 3 shows the results of this questionnaire. The lower the score, the greater the impact of RLS on quality of life.

(Abetz L. et al. Validation of the restless legs syndrome quality of life questionnaire. Value in Health, 2005; 8(2): 157-167)

The RLS QoL questionnaire was completed by the investigator at the baseline and Week 4, and 8 visits. The change from baseline to each post-baseline study visit was calculated as an additional efficacy endpoint.

Sleep Scale:

The Sleep Scale is a 12-item scale that provides a comprehensive view across almost all dimensions of sleep including daytime somnolence, sleep disturbance, sleep adequacy and sleep quantity. The investigator scored subjects on this scale at the baseline and Week 4, and 8 visits. The change from baseline to each post-baseline study visit was calculated as a secondary efficacy endpoint. (Hays, R. D. & Steward, A. L. (1992). Sleep measures. In A. L. Stewart & J. E. Ware (eds.), Measuring functioning and well-being: The Medical Outcomes Study approach (pp. 235-259), Durham, NC: Duke University Press.

Tables 4-12 show the results of the Sleep Rating Scale and change from baseline over time for each of the 9 dimensions scored by the Sleep Rating Scale. N is the number of participants in the study. A low score indicates the absence of problems and a high score indicates a very severe problem.

TABLE 3

Descriptive Statistics of IRLS QoL Rating Scale and Change from Baseline Over Time

| | IRLS QoL Total | | | | | | IRLS QoL Total (Absolute Change) | | | | | | IRLS QoL Total (Percent Change) | | | | |
|---|---|---|---|---|---|---|---|---|---|---|---|---|---|---|---|---|---|
| Week | N | Mean | SD | Min | Median | Max | N | Mean | SD | Min | Median | Max | N | Mean | SD | Min | Median | Max |
| BASELINE | 2 | 46.25 | 30.05 | 25.00 | 46.25 | 67.50 | 2 | 0.00 | 0.00 | 0.00 | 0.00 | 0.00 | 2 | 0.00 | 0.00 | 0.00 | 0.00 | 0.00 |
| VISIT WEEK 4 | 2 | 62.92 | 41.84 | 33.33 | 62.92 | 92.50 | 2 | 16.67 | 11.79 | 8.33 | 16.67 | 25.00 | 2 | 35.19 | 2.62 | 33.33 | 35.19 | 37.04 |
| VISIT WEEK 8 | 1 | 92.50 | | 92.50 | 92.50 | 92.50 | 1 | 25.00 | | 25.00 | 25.00 | 25.00 | 1 | 37.04 | | 37.04 | 37.04 | 37.04 |

TABLE 4

Descriptive Statistics of Sleep Rating Scale and Change from Baseline Over Time

| | Sleep Disturbance Scale | | | | | | Sleep Disturbance (Absolute Change) | | | | | | Sleep Disturbance (Percent Change) | | | | | |
|---|---|---|---|---|---|---|---|---|---|---|---|---|---|---|---|---|---|---|
| Week | N | Mean | SD | Min | Median | Max | N | Mean | SD | Min | Median | Max | N | Mean | SD | Min | Median | Max |
| BASELINE | 2 | 41.25 | 5.30 | 37.50 | 41.25 | 45.00 | 2 | 0.00 | 0.00 | 0.00 | 0.00 | 0.00 | 2 | 0.00 | 0.00 | 0.00 | 0.00 | 0.00 |
| VISIT WEEK 4 | 2 | 33.75 | 15.91 | 22.50 | 33.75 | 45.00 | 2 | −7.50 | 10.61 | −15.00 | −7.50 | 0.00 | 2 | −20.00 | 28.28 | −40.00 | −20.00 | 0.00 |
| VISIT WEEK 8 | 1 | 21.25 | | 21.25 | 21.25 | 21.25 | 1 | −16.25 | | −16.25 | −16.25 | −16.25 | 1 | −43.33 | | −43.33 | −43.33 | −43.33 |

TABLE 5

Descriptive Statistics of Sleep Rating Scale and Change from Baseline Over Time

| | Snoring Scale | | | | | | Sleep Snoring (Absolute Change) | | | | | | Sleep Snoring (Percent Change) | | | | | |
|---|---|---|---|---|---|---|---|---|---|---|---|---|---|---|---|---|---|---|
| Week | N | Mean | SD | Min | Median | Max | N | Mean | SD | Min | Median | Max | N | Mean | SD | Min | Median | Max |
| BASELINE | 2 | 40.00 | 56.57 | 0.00 | 40.00 | 80.00 | 2 | 0.00 | 0.00 | 0.00 | 0.00 | 0.00 | 1 | 0.00 | | 0.00 | 0.00 | 0.00 |
| VISIT WEEK 4 | 2 | 40.00 | 56.57 | 0.00 | 40.00 | 80.00 | 2 | 0.00 | 0.00 | 0.00 | 0.00 | 0.00 | 1 | 0.00 | | 0.00 | 0.00 | 0.00 |
| VISIT WEEK 8 | 1 | 100.00 | | 100.00 | 100.00 | 100.00 | 1 | 20.00 | | 20.00 | 20.00 | 20.00 | 1 | 25.00 | | 25.00 | 25.00 | 25.00 |

TABLE 6

Descriptive Statistics of Sleep Rating Scale and Change from Baseline Over Time

| | Short of Breath Scale | | | | | | Sleep Short of Breath (Absolute Change) | | | | | | Sleep Short of Breath (Percent Change) | | | | | |
|---|---|---|---|---|---|---|---|---|---|---|---|---|---|---|---|---|---|---|
| Week | N | Mean | SD | Min | Median | Max | N | Mean | SD | Min | Median | Max | N | Mean | SD | Min | Median | Max |
| BASELINE | 2 | 0.00 | 0.00 | 0.00 | 0.00 | 0.00 | 2 | 0.00 | 0.00 | 0.00 | 0.00 | 0.00 | 0 | | | | | |
| VISIT WEEK 4 | 2 | 0.00 | 0.00 | 0.00 | 0.00 | 0.00 | 2 | 0.00 | 0.00 | 0.00 | 0.00 | 0.00 | 0 | | | | | |
| VISIT WEEK 8 | 1 | 0.00 | | 0.00 | 0.00 | 0.00 | 1 | 0.00 | | 0.00 | 0.00 | 0.00 | 0 | | | | | |

TABLE 7

Descriptive Statistics of Sleep Rating Scale and Change from Baseline Over Time

| | Sleep Adequacy | | | | | | Sleep Adequacy (Absolute Change) | | | | | | Sleep Adequacy (Percent Change) | | | | | |
|---|---|---|---|---|---|---|---|---|---|---|---|---|---|---|---|---|---|---|
| Week | N | Mean | SD | Min | Median | Max | N | Mean | SD | Mitt | Median | Max | N | Mean | SD | Min | Median | Max |
| BASELINE | 2 | 40.00 | 28.28 | 20.00 | 40.00 | 60.00 | 2 | 0.00 | 0.00 | 0.00 | 0.00 | 0.00 | 2 | 0.00 | 0.00 | 0.00 | 0.00 | 0.00 |
| VISIT WEEK 4 | 2 | 55.00 | 49.50 | 20.00 | 55.00 | 90.00 | 2 | 15.00 | 21.21 | 0.00 | 15.00 | 30.00 | 2 | 25.00 | 35.36 | 0.00 | 25.00 | 50.00 |
| VISIT WEEK 8 | 1 | 100.00 | | 100.00 | 100.00 | 100.00 | 1 | 40.00 | | 40.00 | 40.00 | 40.00 | 1 | 66.67 | | 66.67 | 66.67 | 66.67 |

TABLE 8

Descriptive Statistics of Sleep Rating Scale and Change from Baseline Over Time

| Week | \multicolumn{6}{c|}{Somnolence Scale} | \multicolumn{6}{c|}{Sleep Somnolence (Absolute Change)} | \multicolumn{6}{c|}{Sleep Somnolence (Percent Change)} |

| Week | N | Mean | SD | Min | Median | Max | N | Mean | SD | Min | Median | Max | N | Mean | SD | Min | Median | Max |
|---|---|---|---|---|---|---|---|---|---|---|---|---|---|---|---|---|---|---|
| BASELINE | 2 | 40.00 | 37.71 | 13.33 | 40.00 | 66.67 | 2 | 0.00 | 0.00 | 0.00 | 0.00 | 0.00 | 2 | 0.00 | 0.00 | 0.00 | 0.00 | 0.00 |
| VISIT WEEK 4 | 2 | 40.00 | 47.14 | 6.67 | 40.00 | 73.33 | 2 | −0.00 | 9.43 | −6.67 | −0.00 | 6.67 | 2 | −20.00 | 42.43 | −50.00 | −20.00 | 10.00 |
| VISIT WEEK 8 | 1 | 13.33 | | 13.33 | 13.33 | 13.33 | 1 | 0.00 | | 0.00 | 0.00 | 0.00 | 1 | 0.00 | | 0.00 | 0.00 | 0.00 |

TABLE 9

Descriptive Statistics of Sleep Rating Scale and Change from Baseline Over Time

| Week | N | Mean | SD | Min | Median | Max | N | Mean | SD | Min | Median | Max | N | Mean | SD | Min | Median | Max |
|---|---|---|---|---|---|---|---|---|---|---|---|---|---|---|---|---|---|---|
| | \multicolumn{6}{c|}{Sleep Problems Index I} | \multicolumn{6}{c|}{Sleep Problems Index I (Absolute Change)} | \multicolumn{6}{c|}{Sleep Problems Index I (Percent Change)} |
| BASELINE | 2 | 33.33 | 23.57 | 16.67 | 33.33 | 50.00 | 2 | 0.00 | 0.00 | 0.00 | 0.00 | 0.00 | 2 | 0.00 | 0.00 | 0.00 | 0.00 | 0.00 |
| VISIT WEEK 4 | 2 | 26.67 | 33.00 | 3.33 | 26.67 | 50.00 | 2 | −6.67 | 9.43 | −13.33 | −6.67 | 0.00 | 2 | −40.00 | 56.57 | −80.00 | −40.00 | 0.00 |
| VISIT WEEK 8 | 1 | 0.00 | | 0.00 | 0.00 | 0.00 | 1 | −16.67 | | −16.67 | −16.67 | −16.67 | 1 | −100.00 | | −100.0 | −100.00 | −100.00 |

TABLE 10

Descriptive Statistics of Sleep Rating Scale and Change from Baseline Over Time

| Week | N | Mean | SD | Min | Median | Max | N | Mean | SD | Min | Median | Max | N | Mean | SD | Min | Median | Max |
|---|---|---|---|---|---|---|---|---|---|---|---|---|---|---|---|---|---|---|
| | \multicolumn{6}{c|}{Sleep Problems Index II} | \multicolumn{6}{c|}{Sleep Problems Index II (Absolute Change)} | \multicolumn{6}{c|}{Sleep Problems Index II (Percent Change)} |
| BASELINE | 2 | 40.56 | 18.07 | 27.78 | 40.56 | 53.33 | 2 | 0.00 | 0.00 | 0.00 | 0.00 | 0.00 | 2 | 0.00 | 0.00 | 0.00 | 0.00 | 0.00 |
| VISIT WEEK 4 | 2 | 33.89 | 27.50 | 14.44 | 33.89 | 53.33 | 2 | −6.67 | 9.43 | −13.33 | −6.67 | 0.00 | 2 | 24.00 | 33.94 | −48.00 | −24.00 | 0.00 |
| VISIT WEEK 8 | 1 | 11.67 | | 11.67 | 11.67 | 11.67 | 1 | −16.11 | | −16.11 | −16.11 | −16.11 | 1 | −58.00 | | −58.00 | −58.00 | −58.00 |

TABLE 11

Descriptive Statistics of Sleep Rating Scale and Change from Baseline Over Time

| Week | N | Mean | SD | Min | Median | Max | N | Mean | SD | Min | Median | Max | N | Mean | SD | Min | Median | Max |
|---|---|---|---|---|---|---|---|---|---|---|---|---|---|---|---|---|---|---|
| | \multicolumn{6}{c|}{Sleep Quantity (raw score)} | \multicolumn{6}{c|}{Sleep Quantity (Absolute Change)} | \multicolumn{6}{c|}{Sleep Quantity (Percent Change)} |
| BASELINE | 1 | 7.00 | | 7.00 | 7.00 | 7.00 | 1 | 0.00 | | 0.00 | 0.00 | 0.00 | 1 | 0.00 | | 0.00 | 0.00 | 0.00 |
| VISIT WEEK 4 | 1 | 7.00 | | 7.00 | 7.00 | 7.00 | 1 | 0.00 | | 0.00 | 0.00 | 0.00 | 1 | 0.00 | | 0.00 | 0.00 | 0.00 |
| VISIT WEEK 8 | 1 | 7.00 | | 7.00 | 7.00 | 7.00 | 1 | 0.00 | | 0.00 | 0.00 | 0.00 | 1 | 0.00 | | 0.00 | 0.00 | 0.00 |

TABLE 12

Descriptive Statistics of Sleep Rating Scale and Change from Baseline Over Time

| Week | Optimal Sleep Scale | | | | | | Optimal Sleep (Absolute Change) | | | | | | Optimal Sleep (Percent Change) | | | | | |
|---|---|---|---|---|---|---|---|---|---|---|---|---|---|---|---|---|---|---|
|  | N | Mean | SD | Min | Median | Max | N | Mean | SD | Min | Median | Max | N | Mean | SD | Min | Median | Max |
| BASELINE | 1 | 1.00 |  | 1.00 | 1.00 | 1.00 | 1 | 0.00 |  | 0.00 | 0.00 | 0.00 | 1 | 0.00 |  | 0.00 | 0.00 | 0.00 |
| VISIT WEEK 4 | 1 | 1.00 |  | 1.00 | 1.00 | 1.00 | 1 | 0.00 |  | 0.00 | 0.00 | 0.00 | 1 | 0.00 |  | 0.00 | 0.00 | 0.00 |
| VISIT WEEK 8 | 1 | 1.00 |  | 1.00 | 1.00 | 1.00 | 1 | 0.00 |  | 0.00 | 0.00 | 0.00 | I | 0.00 |  | 0.00 | 0.00 | 0.00 |

CONCLUSION

To date, 2 subjects have been enrolled in this open label pilot study of rasagiline's efficacy in Restless Legs Syndrome. These subjects had a mean baseline IRLS Rating Scale score of 32. After 2 weeks the mean score had decrease to 29. At 4 weeks, one subject had a score of 13 (indicating a 50% decrease from baseline). Another subject discontinued participation in the study, at week 4, with a score of 38, unchanged from this subject's baseline score. By 8 weeks, the remaining subject's IRLS score had decreased to 12 (a 54% decrease from baseline). Additionally, by eight weeks this subject had indicated that the RLS symptoms were "Very Much Improved" on the CGI-I rating scale. Also, by eight weeks this subject had an improvement of 37% in the IRLS Quality of Life Questionnaire compared to baseline. In addition, by eight weeks, this subject had an improvement of 58% in the Sleep Problems Index II statistic measured as part of the Sleep Scale. In summary, in at least a subset of RLS patients, rasagiline has been shown to have a clinically significant effect on the symptoms of RLS.

What is claimed is:

1. A pharmaceutical composition comprising in unit dosage form an amount of R(+)-N-propargyl-1-aminoindan or a pharmaceutically acceptable salt thereof and an amount of pramipexole, wherein the amount of R(+)-N-propargyl-1-aminoindan or of the pharmaceutically acceptable salt thereof is from 0.5 mg to 1.66 mg and wherein the amount of pramipexole is from 0.125 mg to 0.6 mg.

2. The pharmaceutical composition of claim 1, wherein the amount of R(+)-N-propargyl-1-aminoindan is 0.5 mg.

3. The pharmaceutical composition of claim 1, wherein the amount of R(+)-N-propargyl-1-aminoindan is 1 mg.

4. The pharmaceutical composition of claim 1, wherein the R(+)-N-propargyl-1-aminoindan is the pharmaceutically acceptable salt of R(+)-N-propargyl-1-aminoindan.

5. The pharmaceutical composition of claim 4, wherein the pharmaceutically acceptable salt is esylate, mesylate, sulfate or tartrate.

6. The pharmaceutical composition of claim 4, wherein the pharmaceutically acceptable salt is mesylate.

7. The pharmaceutical composition of claim 6, wherein the amount of the pharmaceutically acceptable mesylate salt of R(+)-N-propargyl-1-aminoindan is 1.66 mg.

8. The pharmaceutical composition of claim 1, wherein the amount of pramipexole is from 0.375 mg to 0.6 mg.

9. The pharmaceutical composition of claim 1, wherein the amount of pramipexole is 0.6 mg.

10. The pharmaceutical composition of claim 1, wherein the pramipexole is in a pharmaceutically acceptable salt form.

11. The pharmaceutical composition of claim 10, wherein the pharmaceutically acceptable salt form is pramipexole dihydrochloride.

12. The pharmaceutical composition of claim 11, wherein the amount of pramipexole dihydrochloride is 0.6 mg.

13. The pharmaceutical composition of claim 3, wherein the amount of pramipexole is from 0.125 mg to 0.6 mg.

14. The pharmaceutical composition of claim 3, wherein the amount of pramipexole is from 0.375 mg to 0.6 mg.

15. The pharmaceutical composition of claim 3, wherein the amount of pramipexole is 0.6 mg.

16. The pharmaceutical composition of claim 3, wherein the pramipexole is in a pharmaceutically acceptable salt form.

17. The pharmaceutical composition of claim 16, wherein the pharmaceutically acceptable salt form is pramipexole dihydrochloride.

18. The pharmaceutical composition of claim 17, wherein the amount of pramipexole dihydrochloride is 0.6 mg.

* * * * *